United States Patent [19]

Samson et al.

[11] Patent Number: 4,641,654

[45] Date of Patent: Feb. 10, 1987

[54] STEERABLE BALLOON DILATATION CATHETER ASSEMBLY HAVING DYE INJECTION AND PRESSURE MEASUREMENT CAPABILITIES

[75] Inventors: Wilfred J. Samson, Saratoga; Jeffrey S. Frisbie, San Jose, both of Calif.

[73] Assignee: Advanced Cardiovascular Systems, Inc., Mountain View, Calif.

[21] Appl. No.: 760,722

[22] Filed: Jul. 30, 1985

[51] Int. Cl.$^4$ ............................................. A61M 29/02
[52] U.S. Cl. ..................................... 128/344; 604/95; 128/657
[58] Field of Search ................................. 604/95–103, 604/170, 280; 128/344, 656–658

[56] References Cited

U.S. PATENT DOCUMENTS

| | | | |
|---|---|---|---|
| 4,413,989 | 11/1983 | Schjeldahl et al. | 604/96 |
| 4,467,790 | 8/1984 | Schiff | 128/344 X |
| 4,526,175 | 7/1985 | Chin et al. | 128/344 |
| 4,545,390 | 10/1985 | Leary | 128/772 |

*Primary Examiner*—Dalton L. Truluck
*Attorney, Agent, or Firm*—Flehr, Hohbach, Test, Albritton & Herbert

[57] ABSTRACT

Steerable balloon dilatation catheter assembly having dye injection and pressure measurement capabilities and comprising an elongate flexible tubular member having first and second lumens extending therethrough and a balloon carried by the distal portion of the tubular member and having its interior in communication with the second lumen. A guide wire extends through the first lumen and has a coil carried by the distal portion thereof and extending beyond the distal extremity of the tubular member. A device is coupled to the guide wire facilitating at least limited rotation of the distal extremity of the guide wire. A first fitting is coupled to the second lumen and is adapted to receive a liquid for inflating and deflating the balloon. A second fitting is in communication with the first lumen. The first lumen and the guide wire being sized so that dye injections and/or pressure measurements can be made through the second fitting.

15 Claims, 4 Drawing Figures

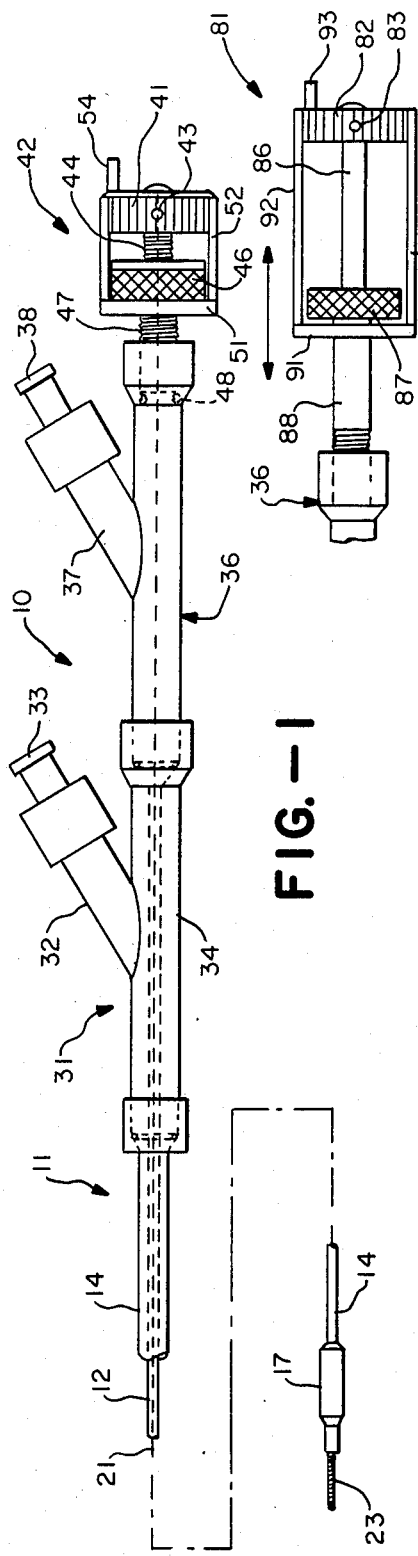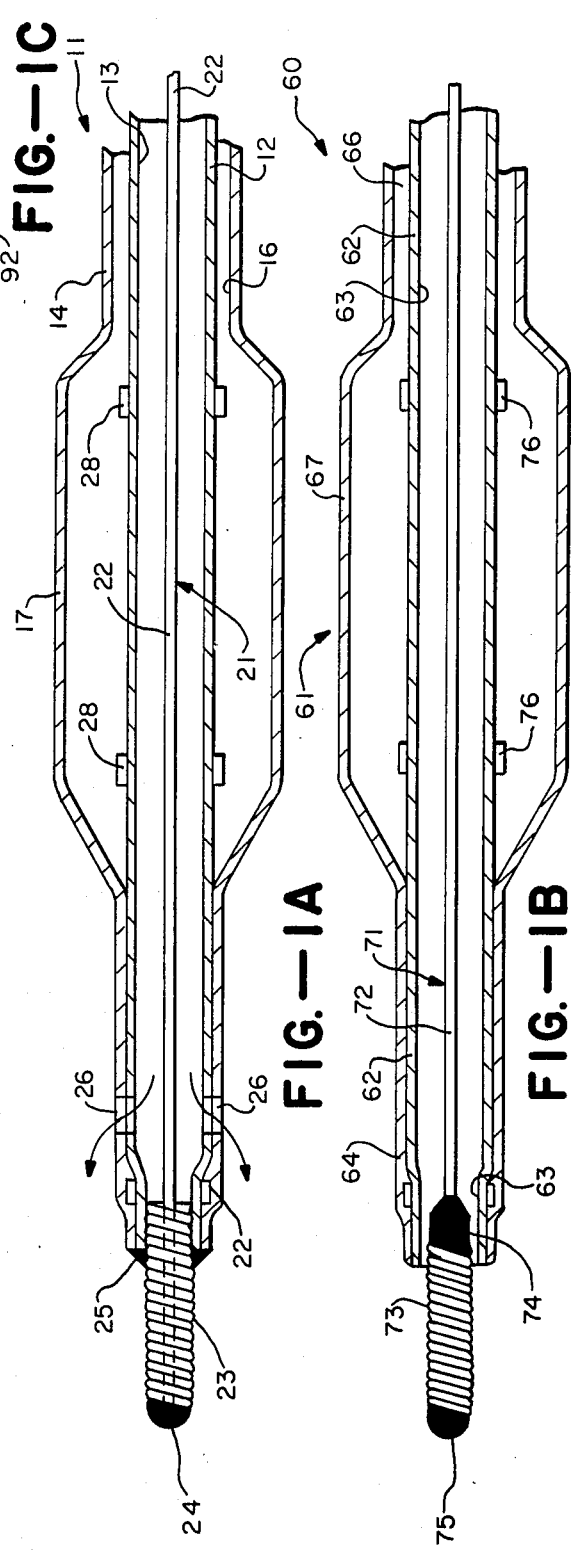

STEERABLE BALLOON DILATATION CATHETER ASSEMBLY HAVING DYE INJECTION AND PRESSURE MEASUREMENT CAPABILITIES

This invention relates to balloon dilatation catheters and more particularly to steerable balloon dilatation catheter assemblies having dye injection and pressure measurement capabilities.

Heretofore there have been provided steerable balloon dilatation catheters. However, with respect to such catheters, it has been found that the space available in the lumen carrying the guide wire utilized for steering is inadequate for introducing dye and for making pressure measurements, particularly with respect to low profile balloon dilatation catheters. There is therefore a need for a new and improved steerable balloon dilatation catheter which overcomes the above named disadvantages.

In general, it is an object of the present invention to provide a steerable balloon dilatation catheter assembly which has dye injection and pressure measurement capabilities.

Another object of the invention is to provide a dilatation catheter assembly of the above character which incorporates a guide wire for steering the same.

Another object of the invention is to provide a dilatation catheter assembly of the above character in which the guide wire is freely rotatable with respect to the distal extremity of the catheter.

Another object of the invention is to provide a dilatation catheter assembly of the above character in which the guide wire is bonded to the distal extremity of the catheter.

Additional objects and features of the invention will appear from the following description in which the preferred embodiments are set forth in detail in conjunction with the accompanying drawings.

FIG. 1 is a side elevational view of a balloon dilatation catheter assembly incorporating the present invention.

FIG. 1A is an enlarged cross sectional view of the distal extremity of the catheter shown in FIG. 1.

FIG. 1B is a cross sectional view similar to FIG. 1A showing a modification of the catheter.

FIG. 1C is a partial side elevational view showing a modification of the rotation device shown in FIG. 1.

In general, the steerable balloon dilatation catheter assembly of the present invention has dye injection and pressure measurement capabilities. It is provided with an elongate flexible tubular member having first and second lumens extending therethrough. A balloon is carried by the distal portion of the tubular member and has its interior in communication with the second lumen.

A guide wire extends through the first lumen and has a coil carried by the distal portion thereof and extends beyond the distal extremity of the tubular member. Means is coupled to the guide wire facilitating at least limited rotation of the distal extremity of the guide wire. A first fitting is coupled to the second lumen and is adapted to receive a liquid for inflating and deflating the balloon. A second fitting is in communication with the first lumen. The first lumen and the guide wire are sized so that dye injections and/or pressure measurements can be made through the second fitting.

More in particular as shown in FIGS. 1 and 1A there is provided a steerable balloon dilatation catheter assembly 10 which is comprised of a flexible elongate member 12 that consists of a first flexible elongate tubular element 12 which is provided with a first lumen 13 extending therethrough and a second flexible elongate flexible tubular element 14 which extends over the first elongate tubular element 12 and forms therewith a second lumen 16 extending longitudinally of the tubular elements 12 and 14. The flexible elongate tubular elements 12 and 14 are formed of a suitable flexible thermo-plastic material such as a polyolefin or polyvinylchloride.

A balloon 17 is carried by the distal portion of the tubular member 14 and more particularly by the second tubular element 14. The balloon has its interior in communication with the second lumen 16. As shown the balloon 17 can be formed integral with the second tubular element 14. The distal extremities of the first and second tubular elements 12 and 14 are bonded together in a suitable manner so as to form a liquid-tight seal between the same. Typically this can be accomplished by inserting a mandrel (not shown) into the distal extremity of the first tubular element 12 in the lumen 13 and applying heat to he distal extremity of the elongate tubular element 14 to cause it to form the liquid-tight seal between the distal extremities of the elements 12 and 14.

A guide wire 21 extends through the first lumen 13. The guide wire 21 consists of an elongate element 22 formed of a suitable material such as stainless steel. It also consists of a coil 23 formed of a suitable radiopaque material such as a platinum alloy which has its distal extremity secured to he distal extremity of the elongate guide wire element 22 by a hemispherical tip 24 formed of a suitable material such as a gold alloy or solder. The proximal extremity of the coil 23 is bonded to the distal extremity of he first tubular element 12 at 25 by suitable means such as an adhesive. The proximal extremity of the coil 23 is not bonded to the flexible elongate element 22 so that the flexible elongate element 22 can rotate with respect to proximal end of the coil 23.

In order to provide dye injection and pressure measurement capabilities, a plurality of vents or openings 26 are provided in the distal extremities of the first and second tubular elements 12 and 14 remote from the balloon 17 and in relatively close proximity to the coil 23. The openings 26 are spaced circumferentially around the distal extremity of the first and second tubular elements 12 and 14. The size and number of openings 26 are such that the desired dye injection and pressure measurements can be made. By way of example, the two holes 26 which are shown can have a diameter of 0.010 to 0.020 inches. The lumen 13 can have a diameter such as 0.023 inches. Markers 28 in the form of gold bands or a suitable radiopaque material can be provided on the first tubular element 12 within the balloon 17 adjacent the proximal and distal extremities of the balloon.

The dilatation catheter 10 also consists of an adapter 31 which is secured to the second tubular element 14 and is provided with a side arm 32 in communication with the lumen 16. The side arm 32 includes a Luer fitting 33 through which a radiographic contrast liquid can be introduced into the lumen 16 for inflating the balloon.

The first tubular element 12 extends through the central arm 34 of the adapter 31 and is connected to an adapter 36. The adapter 36 is also provided with a side arm 37 which is provided with a Leur fitting 38 through which a dye injection can be made or alternatively pressure measurements can be made. The side arm 37 is in communication with the lumen 13 in the first tubular element 12. The guide wire 21 extends through the adapter 31 and through the adapter 36 and is connected to a thumb screw 41 of a rotation device 42. The guide wire is affixed to the thumb screw 41 by a set screw 43. The thumb screw 41 is provided with a threaded cylindrical extension 44 which is threaded into a knob 46. The knob 46 is provided with a threaded cylindrical extension 47 which is threaded into the adapter 36 and is adapted to engage an O-ring 48 to establish a liquid-tight seal with respect to the guide wire 21. A rotation limiting ring 51 affixed to the distal extremity of arms 52 carried by the thumb screw 41 limits the amount of rotational movement of the thumb screw 41 with respect to the knob 46 and thus limits the amount of rotation which can be supplied to the distal extremity of the guide wire 21. A pin 54 is carried by the thumb screw 41 to facilitate rotation of the thumb screw by a finger of the hand.

Operation and use of the steerable dilatation catheter may now be briefly described as follows. The balloon 17 can be inflated outside of the human body to expel air before introduction into an arterial vessel by introducing radiographic contrast liquid through the side arm 32 to inflate the balloon. After the balloon 17 has been inflated and the air removed therefrom, it can be deflated. The deflated dilatation catheter can then be inserted into the arterial vessel of the human body. It can be guided by use of the guide wire 21 which can be rotated by use of the knob 41 to position the coil 23 by rotation of the distal extremity of the coil 23. If desired, the coil 23, before insertion into the arterial vessel, can be provided with a slight bend so that when it is rotated it will face in different directions. The rotatian limiting device 42 prevents undue stress being placed upon the turns of the helical coil 23 or alternatively, undue wrapping of the balloon 17. Even though the proximal extremity of the coil 23 of the guide wire is attached to the distal extremity of the catheter, it has been found that the guide wire 21 still is very maneuverable through a number of revolutions as determined by the torque limiting device 42 to facilitate steering of the catheter as it is being guided through the arterial vessels of the patient. The coil 23 itself can absorb a number of rotations. The positioning of the catheter can be observed under x-rays by observing the positioning of the coil 23 and also by observing the positioning of the marker rings 28. After the balloon has been positioned in the stenosis in the arterial vessel, the balloon 17 can be expanded or inflated by introducing radiographic contrast liquid through the side arm 32. With the balloon 17 in place, or any other time it is deemed desirable, a distal dye injection can be accomplishedd by inserting the dye through the side arm 37 so that it passes through the lumen 13 after which it passes through the openings 26 on the other side of the stenosis. The distal dye injection makes it possible for the physician to make further observations with respect to the arterial vessel beyond the stenosis where the balloon 17 is positioned. Alternatively, or sequentially, the physician can, also by means of the openings 26, make pressure measurements of the pressure of the blood in the arterial vessel beyond the stenosis in which the balloon 17 is positioned. The diamater of the lumen 13 is adequate to make accurate pressure measurements possible.

After the desired procedures have been accomplished, the dilatation catheter can be removed.

It can be seen that the dilatation catheter 10 provided in FIGS. 1 and 1A provides a complete assembly with a non-removable guide wire. The guide wire extends forwardly of the catheter and provides steerability for the catheter. This steerability is enhanced by the use of the rotation capabilities for the guide wire even though its rotation is limited to prevent undue twisting of the coil 23 or wrapping of the balloon 17. The dye injection capability makes it possible for a physician to visualize the anatomy of the arterial vessel downstream from the balloon. It is also possible to make pressure measurements of the blood in the arterial vessel downstream from the balloon.

Another embodiment of the dilatation catheter assembly incorporating the present invention is shown in FIGS. 1B and 1C. In this embodiment, the dilatation catheter 60 is comprised of a tubular member 61 which consists of a first flexible elongate element 62 having a first lumen 63 extending therethrough. It also consists of a second flexible elongate tubular element 64 which coaxially extends over the first tubular element 62 and forms in conjunction therewith a second lumen 66 extending longitudinally thereof. A balloon 67 is formed integral with the second tubular element 64 and has its interior in communication with the lumen 66. The distal extremities of the first and second tubular elements 62 and 64 are bonded together in the same manner as the distal extremities of the tubular elements 12 and 14.

A guide wire 71 is provided which is similar to the guide wire 21. It is formed of an elongate flexible element 72 of a suitable material such as stainless steel. A coil 73 of a suitable radiopaque material such as platinum alloy has its proximal extremity secured to the element 72 by suitable means such as a gold alloy or solder 74. A hemispherical tip 75 formed of a suitable material such as gold or solder is secured to the distal extremity of the coil 73 and is also secured to the elongate element 72. The lumen 63 can have a suitable diameter such as 0.023 inches and the coil 73 can have a suitable diameter such as 0.016 inches. Markers 76 have been provided on the first tubular element within the confines of the balloon 67 adjacent the proximal and distal extremities of the balloon and serve the same purposes as the markers 28 in the embodiment shown in FIGS. 1 and 1A.

The remaining portions of the catheter 60 are very similar to that shown in FIG. 1 with the exception that a different rotation device 81 is provided in place of the rotation limiting device 42. As shown in FIG. 1C, the guide wire 71 is secured to a knurled knob 82 by a set screw 83. The guide wire 71 extends through a cylindrical extension 86 which can be formed integral with the knob 82. The extension 86 is provided with a smooth outer surface and is slidably mounted in a knob 87 which is provided with a cylindrical extension 88 which is threaded into the adapter 37. Means is provided for limiting the axial movement of the knob 82 with respect to the knob 87 and consists of a stop ring 91 carried by a pair of arms 92 secured to and carried by the knob 82. A pin 93 is carried by the knob 82 and is provided for rotating the knob 82 and the guide wire attached thereto.

Operation and use of the catheter 60 shown in FIG. 1B may now be briefly described as follows. The operation of the catheter 60 is very similar to that described with respect to he catheters shown in FIGS. 1 and 1A with the exception that the guide wire 71 is freely rotatable with respect to the catheter 60. In the embodiment shown in FIGS. 1 and 1A, the rotation of the guide wire 21 is limited by the rotation limiter 42. In the present embodiment, the rotation is unlimited. Also, in the present embodiment the guide wire 71 can be advanced and retracted with respect to the catheter 60 which is not possible with respect to the guide wire 21 shown in FIGS. 1 and 1A. The advancement and retraction of the guide wire 71 is limited to the length of the arms 92. The innermost position is reached when knob 82 engages the top side of the knob 87 and the outermost position is reached the ring engages the udnerside of knob 87. The guide wire 71 can be used to position the catheter in the arterial vessel. In addition, after the balloon has been inflated in the stenosis, distal dye injections can be accomplished merely by advancing the coil 73 so that it is free of the lumen 63. Thereafter distal dye injections and pressure measurements may be made through the lumen 63. The size of the elongate element 72 of the guide wire 71 is sufficiently small so that such pressure measurements and distal dye injections can be made readily through the lumen 63.

It is apparent from the foregoing that there has been provided a dilatation catheter which makes possible distal dye injections and/or pressure measurements beyond the balloon dilatation which also incorporates a guide wire to facilitate steering of the catheter. In one embodiment the guide wire is fixed with respect to relative longitudinal movement between the guide wire and the catheter but is rotatable through a limited number of rotations and in the other embodiment the guide wire is freely rotatable and, in addition, is extensible relative to the catheter for a limited distance.

What is claimed is:

1. In a steerable balloon dilatation catheter assembly having dye injection and pressure measurement capabilities, an elongate flexible tubular member having first and second lumens extending longitudinally thereof a balloon carried by the distal portion of the tubular member and having its interior in communication with the second lumen, the first lumen extending through the balloon and being open at its distal extremity a guide wire extending through the first lumen and having a coil carried by the distal portion thereof and extending beyond the distal extremity of the tubular member, means coupled to the guide wire facilitating at least limited rotation of the distal extremity of the guide wire, means coupled to the guide wire limiting inward and outward movement of the guide wire in a direction longitudinal of the axis of rotation of the guide wire, a first fitting coupled to the second lumen and adapted to receive a liquid for inflating and deflating the balloon and a second fitting in communication with the first lumen, said first lumen and said guide wire being sized so that dye injections and/or pressure measurements can be made through the second fitting.

2. A catheter assembly as in claim 1 wherein the coil of said guide wire is rotatable with respect to the distal extremity of the tubular member and is extensible with respect to the tubular member.

3. A catheter assembly as in claim 1 wherein said guide wire includes an elongate flexible element extending through the tubular member and to the distal extremity of the coil and a hemispherical tip bonding the distal extremities of the flexible elongate element and the coil to each other.

4. A catheter assembly as in claim 1 wherein said means for limiting movement of the guide wire in a direction longitudinal of the axis of rotation includes a fixed member, a knob secured to the guide wire and means carried by the knob and adapted to engage the fixed member to limit inward and ouward movement with respect to the fixed member.

5. In a steerable balloon dilatation catheter assembly having dye injection and pressure measurement capabilities, a first elongate flexible tubular member having a lumen extending, therethrough and being open at the distal extremity of the first tubular member, a second elongate flexible tubular element and forming between the first and second tubular elements an annular lumen extending longitudinally of the first and second tubular elements, a balloon carried by the second tubular element and having its interior in communication with the lumen extending between the first and second tubular elements, a guide wire extending through the lumen of the first tubular element and having a coil carried by the distal extremity thereof and extending beyond the distal extremity of the first and second tubular elements, means coupled to the guide wire facilitating at least limited rotation of the distal extremity of toh guide wire and limiting inward and ouward movement of the guide wire in a direction longitudinal of the axis of rotation of the guide wire, a first fitting coupled to the lumen extending between the first and second tubular elements and adapted to receive a liquid for inflating and deflating the balloon, a second fitting in communication with the lumen in the first tubular element, said first lumen in said first tubular element and said guide wire being sized so that dye injections and/or pressure measurements can be made through the second fitting.

6. A catheter assembly as in claim 5 wherein the coil of said guide wire is rotatable with respect to the distal extremities of the first and second elongate elements and is extensible with respect to the first and second elongate elements.

7. A catheter assembly as in claim 1 wherein said means for limiting the inward and outward movement of the guided wire includes a fixed member, a knob secured to the guide wire and means carried by the knob and adapterd to engage the fixed member to limit inward and outward movement with respect to the fixed member.

8. A catheter assembly as in claim 7 wherein said means for limiting movement of the guide wire includes an additional knob carried by the first tubular element, an extension carried by the first named knob and slidably mounted in the additional knob and a ring carried by the first named knob and spaced a predetermined distance from the first named knob and beyond the additional knob.

9. A catheter assembly as in claim 5 wherein the guide wire includes an elongate flexible element extending through the first tubular element and to the distal extremity of the coil and a hemispherical tip bonding the distal extremities of the flexible elongate element and the coil to each other.

10. In a steerable balloon dilatation catheter assembly having dye injection and pressure measurement capabilities, an elongate flexible tubular member having first and second lumens extending longitudinally thereof, a balloon carried by the distal portion of the tubular member and having its interior in communication with the second lumen, a guide wire extending through the first lumen and having a coil carried by the distal portion thereof and extending beyond the distal extremity of the tubular member, means coupled to the guide wire facilitating at least limited rotation of the distal extremity of the guide wire, a first fitting coupled to the second lumen and adapted to receive a liquid for inflating and deflating the balloon, a second fitting in communication with the first lumen, said first lumen and said guide wire being sized so that dye injections and/or pressure measurements can be made through the second fitting and means bonding the proximal extremity of the coil to the distal extremity of the tubular member, said tubular member having at least one opening remote from the balloon extending from the first lumen to ambient whereby dye injections and pressure measurements can be made through said at least one opening.

11. In a steerable balloon dilatation catheter assembly having dye injection and pressure measurement capabilities, an elongate flexible tubular member having first and second lumens extending therethrough, a balloon carried by the distal portion of the tubular member and having its interior in communication with the second lumen, a guide wire extending through the first lumen and having a coil carried by the distal portion thereof and extending beyond the distal extremity of the tubular member, means coupled to the guide wire facilitating at least limited rotation of the distal extremity of the guide wire, a first fitting coupled to the second lumen and adapted to receive a liquid for inflating and deflating the balloon and a second fitting in communication with the first lumen, said first lumen and said guide wire being sized so that dye injections and/or pressure measurements can be made through the second fitting, said guide wire including an elongate flexible element extending through the tubular member and to the distal extremity of the coil and a hemispherical tip bonding the distal extremities of the flexible elongate element and the coil to each other, the flexible elongate element of the guide wire being free to rotate with respect to the proximal extremity of the coil.

12. In a steerable balloon dilatation catheter assembly having dye injection and pressure measurement capabilities, an elongate flexible tubular member having first and second lumens extending, longitudinally thereof, a balloon carried by the distal portion of the tubular member and having its interior in communication with the second lumen, a guide wire extending through the first lumen and having a coil carried by the distal potion thereof and extending beyond the distal extremity of the tubular member, means coupled to the guide wire facilitating at least limited rotation of the distal extremity of the guide wire, a first fitting coupled to the second lumen and adapted to receive a liquid for inflating and deflating the balloon and a second fitting in communication with the first lumen, said first lumen and said guide wire being sized so that dye injections and/or pressure measurements can be made through the second fitting, said guide wire including an elongate flexible element extending through the tubular member and to the distal extremity of the coil and a hemispherical tip bonding the distal extremities of the flexible elongate element and the coil to each other, the proximal extremity of the coil being bonded to the tubular member.

13. In a steerable balloon dilatation catheter assembly having dye injection and paressure measurement capabilities, a first elongate flexible tubular member having a lumen extending therethrough, a second elongate flexible tubular element and forming between the first and second tubular elements an annular lumen extending longitudinally of the first and second tubular elements, a balloon carried by the second tubular elements and having its interior in communication with the lumen extending between the first and second tubular elements, a guide wire extending through the lumen of the first tubular element and having a coil carried by the distal extremity thereof and extending beyond the distal extremity of the first and second tubular elements, means coupled to the guide wire facilitating at least limited rotation of the distal extremity of the guide wire, a first fitting coupled to the lumen extending between the first and second tubular elements and adapted to receive a liquid for inflating and deflating the balloon, a second fitting in communication with the lumen in the first tubular element, said first lumen in said first tubular element and said guide wire being sized so that dye injections and/or pressure measurements can be made through the second fitting and means for bonding the proximal extremity of the coil to the distal extremity of the first tubular element, said first and second tubular elements having at least one opening remote from the balloon extending from the lumen in the first tubular element to ambient whereby dye injections and pressure measurements can be made through said opening.

14. In a steerable balloon dilatation catheter assembly having dye injection and pressure measurement capabilities, a first elongate flexible tubular member having a lumen extending therethrough, a second elongate flexible tubular element and forming between the first and second tubular elements and annular lumen extending longitudinally of the first and second tubular elements, a balloon carried by the second tubular elements and having its interior in communication with the lumen extending between the first and second tubular elements, a guide wire extending through the lumen of the first tubular element and having a coil carried by the distal extremity thereof and extending beyond the distal extremity of the first and second tubular elements, means coupled to the guide wire facilitating at least limited rotation of the distal extremity of the guide wire, a first fitting coupled to the lumen extending between the first and second tubular elements and adapted to receive a liquid for inflating and deflating the balloon, a second fitting in communication with the lumen in the first tubular element, said first lumen in said first tubular element and said guide wire being sized so that dye injections and/or pressure measurements can be made through the second fitting, the guide wire including an elongate flexible element extending through the first tubular element and to the distal extremity of the coil and a hemispherical tip bonding the distal extremities of the flexible elongate element and the coil to each other, the flexible elongate element of the guide wire being free to rotate with respect to the proximal extremity of the coil.

15. In a steerable balloon dilatation catheter assembly having dye injection and pressure measurement capabilities, a first elongate flexible tubular member having a lumen extending therethrough, a second elongate flexible tubular element and forming between the first and second tubular elements an annular lumen extending longitudinally of the first and second tubular elements, a balloon carried by the second tubular elements and having its interior in communication with the lumen extending between the first and second tubular elelments, a guide wire extending through the lumen of the first tubular element and having a coil carried by the distal extremity thereof and extending beyond the distal extremity of the first and second tubular elements, means coupled to the guide wire facilitating at least limited rotation of the distal extremity of the guide wire, a first fitting coupled to the lumen extending between the first and second tubular elements and adapted to receive a liquid for inflating and deflating the balloon, a second fitting in communication with the lumen in the first tubular element, said first lumen in said first tubular element and said guide wire being sized so that dye injections and/or pressure measurements can be made through the second fitting, the guide wire including an elongate flexible element extending through the first tubular element and to the distal extremity of the coil and a hemispherical tip bonding the distal extremities of the flexible elongate element and the coil to each other, the proximal extremity of the coil being bonded to the tubular member.

* * * * *